United States Patent [19]

Manoury et al.

[11] Patent Number: 4,963,680

[45] Date of Patent: Oct. 16, 1990

[54] PIPERAZINE DERIVATIVES AND THEIR PREPARATION PROCESS

[75] Inventors: Philippe Manoury, Verrieres le Buisson; Jean Binet, Breuillet; Daniel Obitz, Fontenay aux Roses; Gerard Defosse, Paris; Elisabeth Dewitte, Saint Gratien; Corinne Veronique, Villejuif, all of France

[73] Assignee: Synthelabo, Paris, France

[21] Appl. No.: 388,374

[22] Filed: Aug. 2, 1989

[30] Foreign Application Priority Data

Aug. 3, 1988 [FR] France .................. 88 10481

[51] Int. Cl.$^5$ .................. C07D 295/08; C07D 295/10
[52] U.S. Cl. .................. 544/395; 544/389; 544/392; 544/394
[58] Field of Search ............ 544/389, 392, 394, 395, 544/403

[56] References Cited

U.S. PATENT DOCUMENTS

| | | | |
|---|---|---|---|
| 3,812,127 | 5/1974 | Moyer | 260/980 |
| 4,518,712 | 5/1985 | Fujimura et al. | 544/392 |
| 4,686,220 | 8/1987 | Medwid et al. | 544/392 |
| 4,692,525 | 9/1987 | Bonacchi et al. | 544/360 |
| 4,845,221 | 7/1989 | Stack et al. | 544/393 |

FOREIGN PATENT DOCUMENTS 89470 5/1985 Japan .................. 544/360

OTHER PUBLICATIONS

Ivanov et al., Chem. Abst. 88–89624u (1977).
Dantchev. et al., Chem. Abst. 88–6589n (1977).
Khristova et al., Chem. Abst. 101–222109k (1984).
Drandarov et al., Chem. Abst. 100–197839t (1984).
Christova et al., Chem. Abst. 94–30049f (1980).
Christova et al., Chem. Abst. 90–87114v (1978).

*Primary Examiner*—Cecilia Shen
*Attorney, Agent, or Firm*—Wegner & Bretschneider

[57] ABSTRACT

A piperazine derivative of formula (I)

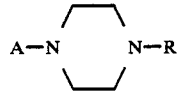

in which:
R is hydrogen or a straight or branched ($C_{1-4}$) alkoxycarbonyl group; and
A is a 7-methoxy-1-naphthalenyl, 6-methoxy-2,3-dihydro-1-(1H)-indenyl or 7-methoxy-1,2,3,4-tetrahydro-1-naphthalenyl group, or an optically active isomer thereof, or a salt thereof.

3 Claims, No Drawings

PIPERAZINE DERIVATIVES AND THEIR PREPARATION PROCESS

The present application relates to piperazine derivatives and to a process for their preparation.

The present invention provides a piperazine derivative of formula (I):

in which:
R is hydrogen or a straight or branched $(C_{1-4})$-alkoxycarbonyl group; and
A is a 7-methoxy-1-naphthalenyl, 6-methoxy-2,3-dihydro-1-(1$\underline{H}$)-indenyl, or 7-methoxy-1,2,3,4-tetrahydro-1-naphthalenyl group, or an optically active isomer thereof, or a salt thereof.

The optically active enantiomers of the derivative of formula (I) containing an asymmetric carbon are part of the invention.

Examples of derivatives of formula (I) are:
1-(7-methoxy-1-naphthalenyl)piperazine,
1-[6-methoxy-2,3-dihydro-1-(1$\underline{H}$)-indenyl]piperazine,
($\pm$)1-(7-methoxy-1,2,3,4-tetrahydro-1-naphthalenyl)-piperazine,
($\pm$)-1-(7-methoxy-1,2,3,4-tetrahydro-1-naphthalenyl)piperazine, or
($-$)-1-(7-methoxy-1,2,3,4-tetrahydro-1-naphthalenyl)piperazine, or a salt thereof.

An example of a salt is a fumarate salt.

The derivatives of the present invention can be prepared according to the reaction diagram given in the appendix.

The present invention also provides a process for the preparation of a derivative of formula (I), or a salt thereof, in which a compound of formula (II) AX, in which A is as defined above and X is a halogen, is reacted with a 1-[(C$_{1-4}$)alkoxycarbonyl]piperazine or a salt thereof, generally in a solvent such as MIBK (methyl isobutyl ketone), and at a temperature from 20° to 120° C. and, if it is wished to obtain a derivative in which R is H, the (C$_{1-4}$)alkoxycarbonyl group R is removed by acid hydrolysis and, if desired, the derivative of formula (I) thus formed is converted to a salt thereof.

The present invention further provides a process for the preparation of a derivative of formula (I), in which A is a 7-methoxy-1-naphthalenyl group and R is hydrogen, in which 7-methoxynaphthalenamine is reacted with the hydrochloride of bis-(2-chloroethyl)amine, and, if desired, the derivative of formula (I) thus obtained is converted to a salt thereof.

The starting compounds of formula (II) are described in the literature (see the Examples).

The derivatives of the invention are synthetic intermediates, which are useful for preparing compounds with a therapeutic activity, certain of which are described in French Patent Application Nos. 88.10482 and 88.13324.

The following Examples further illustrate the invention. The structure of the compounds is confirmed by analysis and IR and NMR spectra.

EXAMPLE 1

1-(7-Methoxy-1-naphthalenyl)piperazine 32 g (0.184 mol) of 7-methoxy-1-naphthalenamine (Helv. Chim. Acta. 30 816-38, 1947) and 32.84 g (0.184 mol) of bis-(2-chloroethyl)amine hydrochloride in solution in 170 ml of butanol are placed in a 500 ml flask, surmounted by a Dean-Stark water separator, provided with a magnetic stirrer and placed under an argon atmosphere. A spatula-point of potassium iodide is added and the reaction mixture is heated to reflux temperature for 20 h. Then 11.6 g (0.092 mol) of potassium carbonate is added and the mixture left to reflux for 10 h. A further 3.87 g (0.03 mol) of the same reagent is added and the mixture left to reflux for a further 8 h. This operation is repeated twice. The reaction mixture is evaporated to dryness and the residue triturated between water and ether; a mauve solid is centrifuged out. 39.2 g (88%) of the hydrochloride of the product is thus obtained.

The base is liberated by stirring the hydrochloride in water, in the presence of 20 ml of 10N caustic soda, and the mixture is extracted with ether. After drying and evaporation of the solvent, the crude oil is distilled, bp (0.1 mm Hg)=about 200° C.

25.5 g (57.2%) of a colourless oil is finally obtained, the NMR spectrum of which confirms its structure.

The fumarate of this base is prepared, and a white solid is obtained; mp 189°–191° C.

EXAMPLE 2

1-[6-Methoxy-2,3-dihydro-1-(1$\underline{H}$)-indenyl]piperazine

2.1 6-Methoxy-2,3-dihydro-1H-indenol 33.5 g (0.2065 mol) of 6-methoxy-2,3-dihydro-1H-indenone is added in portions to a solution of 3.8 g (0.1 mol) of lithium aluminium hydride in 700 ml of dry ether and 50 ml of dry tetrahydrofuran, under an inert atmosphere with cooling. (H.0. House et al. J. Org. Chem. 35 647-51, 1970 and J. Org. Chem. 42, 2155–60, 1977).

After 6 h of reflux the reaction mixture is cooled in ice and hydrolysed. After filtering off the inorganic solid and washing with ether, the filtrate is evaporated to dryness. 33.43 g (98.6%) of a colourless oil which crystallizes spontaneously to a white solid of mp =46 —47° C., is obtained.

2.2 1-Chloro-6-methoxy-2,3-dihydro-1$\underline{H}$-indene

A solution of 2.25 g (0.02 mol) of methanesulphonyl chloride in 2.5 ml of methylene chloride is added little by little to a solution of 1.64 g (0.01 mol) of the compound obtained above in 7.5 ml of methylene chloride and 3.5 ml of pyridine, placed in a bath maintained at 20 C. After stirring for 2.5 h at 20.C., the mixture is thrown onto ice and settled. The organic phase is washed with acidulated water and then water, dried over magnesium sulphate, filtered and concentrated. 1.63 g (89.5%) of the chlorinated derivative is obtained.

2.3. 1-[6-methoxy-2,3-dihydro-1-(1H)-indenyl]piperazine

A solution of 8.32 g (0.0455 mol) of the above chlorinated derivative (2.2) in 40 ml of MIBK is added dropwise to a solution of 16 g (0.0859 mol) of 1,1-dimethylethyl-1-piperazine carboxylate in 80 ml of MIBK. A spatula-point of sodium iodide is added and the reaction mixture is heated to reflux temperature for 15 h. After cooling the crystallized solid is filtered off and rinsed, and then the filtrate is evaporated to dryness. The residue is taken up in water and ether, and the ethereal phase is washed, then dried, filtered and concentrated. 200 ml of 3N hydrochloric acid is added to the residue, which has been taken up in about 100 ml of ether. The mixture is heated to the reflux temperature of the ether. Once the evolution of gas has finished, the aqueous phase is decanted, alkalinized with an excess of caustic soda and then the organic fraction is extracted with ether, washed and the extract is dried. After filtration and concentration 3.6 g (36%) of a crystalline solid is obtained; mp = 102–4° C.

EXAMPLE 3

(±)1-(7-methoxy-1,2,3,4-tetrahydro-1-naphthalenyl)-piperazine 3.1. 1-Chloro-7-methoxy-1,2,3,4-tetrahydronaphthalene 35.6 g (0.2 mol) of 7-methoxy-1,2,3,4-tetrahydro-1-naphthalenol (D.G. Thomas, A.H. Nathan J. Am. Chem. Soc. 79, 331, 1948) are stirred at ambient temperature for 3 hours in a litre of concentrated hydrochloric acid.

The mixture is extracted with hexane, the organic phase is washed with water, dried with magnesium sulphate, filtered and evaporated.

37.7 g (96%) of an oil is obtained, which is used in the crude state for the following reaction. 3.2. 1,1-Dimethylethyl-4-(7-methoxy-1,2,3,4-tetrahydro-1-naphthalenyl)piperazinecarboxylate.

A mixture of 37.7 g (0.19 mol) of the above product and 29.8 g (0.16 mol) of 1,1-dimethylethyl piperazinecarboxylate (L.A. Carpino et coll. J. Org. Chem. 48. 664, 1983) and 55.2 g (0.4 mole) of potassium carbonate in 200 ml of acetone is heated to reflux temperature.

Reflux is maintained for 72 h. The mixture is evaporated, the residue is taken up in water and ether, and then decanted. The ethereal phase is dried, filtered and evaporated. The product is purified by chromatography on a silica column. 38.9 g of oil (70%) is thus obtained.

3.3. (±) 1-(7-Methoxy-1,2,3,4-tetrahydro-1-naphthalenyl)piperazine 39.6 g (0.11 mol) of 1,1-methoxy-4-(1,2,3,4-tetrahydro-1-naphthalenyl)piperazinecarboxylate in 240 ml of 3N hydrochloric acid are heated at 45° C. for 2 hours.

The mixture is extracted with ether. The aqueous phase is alkalinized; the base is extracted into ether. The ether phase is dried, filtered and evaporated.

21 g (75%) of oil is obtained from which the fumarate is prepared; mp=176 ° C.

EXAMPLE 4

(+)1-(7-Methoxy-1,2,3,4-tetrahydro-1-naphthalenyl)-piperazine 81 g (0.33 mol) of (±) 1-(7-methoxy-1,2,3,4-tetrahydro-1-naphthalenyl)piperazine is dissolved while warming in 150 ml of ethanol and 50 g of R(-)mandelic acid. The solution is left to cool and then the precipitate is filtered off.

It is recrystallized from ethanol twice. (+)1-(7-methoxy-1,2,3,4-tetrahydro-1-naphthalenyl)piperazine R(-)mandelate is obtained, mp=174° C., $[\alpha]_D^{20}= +56.1°$, c=2CH$_3$OH. The salt is converted to an oily base $[\alpha]_D^{20} = +153.0°$ , c=14.25 CH$_3$OH. cl

EXAMPLE 5

(−)1−(7-Methoxy-1,2,3,4-tetrahydro-1-naphthalenyl)-piperazine

The preceding ethanolic filtrate (ex. 4) is evaporated, and the residue is taken up in water; the aqueous phase is alkalinized and extracted with ether. The ethereal phase is washed, dried, filtered and evaporated. The oil obtained is dissolved in 90 ml of ethanol and 30 g of S(+)mandelic acid while warming. The mixture is left to cool, and the precipitate is filtered. After two recrystallizations from ethanol, (−)1-(7-methoxy-1,2,3,4-tetrahydro-1-naphthalenyl)piperazine S(+)mandelate is obtained; mp=174° C., $[\alpha]_D^{20}= −58.15°$, c=2CH$_3$OH. For the base $[\alpha]_D^{20}=-153.30°$ c=14.25 CH$_3$OH.

Derivatives of formula (I) of the invention, prepared in the Examples, are represented in the following Table:

TABLE

| Compound | A | mp (°C.) (salt or base) |
|---|---|---|
| 1 | (cyclopentane fused to methoxybenzene with attachment point; OCH$_3$) | 189–91(fumarate) |
| 2 | (7-methoxy-1,2,3,4-tetrahydronaphthalen-1-yl; OCH$_3$) | 102–4(base) |
| 3 | (6-methoxy-1,2,3,4-tetrahydroanthracen-1-yl type; OCH$_3$) | 176(fumarate) |
| 4 | (same as 3; OCH$_3$) | 174 R(−)mandelate of the dextrorotatory isomer |
| 5 | (6-methoxynaphthalen-1-yl; OCH$_3$) | 174 S(+)mandelate of the levorotatory isomer. |

The compounds of the invention are used as intermediates in the preparation of various compounds; in particular for the preparation of compounds of formula:

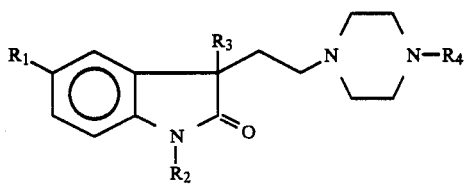

in which:
R₁ is hydrogen, a halogen or a (C₁₋₄)alkyl group;
R₂ is hydrogen or a (C₁₋₄)alkyl group;
R₃ is hydrogen, a (C₁₋₄)alkyl group or a S-(C₁₋₄)alkyl group; and
R₄ is a 7-methoxy-1-naphthalenyl, 6-methoxy-2,3-dihydro-1-(1H)-indenyl or 7-methoxy-1,2,3,4-tetrahydro-1-naphthalenyl group, described in French Patent Application No. 88.10482 and for the preparation of compounds described in French Patent Application No. 88.13324:

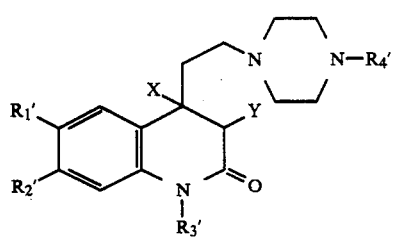

in which:
R'₁ and R'₂ are each, independently of one another, hydrogen, a halogen or a (C₁₋₄)alkyl group;
R'₃ is hydrogen or a (C₁₋₄)alkyl group;
R'₄ is a naphthylenyl or tetrahydronaphthalenyl group, which may be substituted, for example with a methoxy group; and
X and Y are each hydrogen or together form a bond.

These final compounds have pharmacologically useful properties, and are useful for the treatment of migraine, anxiety, depression, obesity, schizophrenia, vascular or gastrointestinal spasms, hypertension and platelet aggregation and are useful as antiemetics.

EXAMPLE 6

5-Fluoro-3-{2-[4-(7-methoxy-1,2,3,4-tetrahydropiperazinyl]ethyl-1-naphthyl)-1-ethyl}-1,3-dihydro-2(2H)-indolone fumarate 3-(Ethylthio)-5-fluoro-3-(2-hydroxyethyl)-1,3-dihydro-2(2H)-indolone A solution of 22.2 g (0.2 mole) of 4-fluoroaniline in 650 ml of methylene chloride is cooled to −65° C. and 21.4 ml of t-butyl hypochlorite, dissolved in 90 ml of CH₂Cl₂, are then added dropwise. The mixture is stirred for ¼ hour after the addition is complete and 26.2 g (0.2 mole) of 3-(ethylthio)-γ-butyrolactone, diluted in 90 ml of CH₂Cl₂, are then added in the course of approximately 1 hour.

The mixture is kept stirred at −65° C. for 2 hours and 27.5 ml of triethylamine, diluted in 90 ml of CH₂Cl₂, are added. The temperature of the mixture is allowed to return to 20° C. and the mixture is left to stand overnight. The reaction mixture is poured into water, settling is allowed to take place, and the organic phase is separated and dried, filtered and evaporated. The resulting solid is purified by chromatography on silica (eluant: ethyl acetate).

3-(Ethylthio)-5-fluoro-3-(2-hydroxyethyl)-1,3-dihydro-2(2H)indolone is obtained.

M.p. 125° C.

3-(Ethylthio)-5-fluoro-3-(2-hydroxyethyl)-1,3-dihydro-2(2H)-indolone tosylate.

A solution of 19 g (0.075 mole) of 3-(ethylthio)-5-fluoro-3-(2-hydroxyethyl)-1,3-dihydro-2(2H)-indolone in 150 ml of pyridine is cooled to approximately 5° C. 15.6 g (0.082 mole) of 4-methylbenzenesulphonyl chloride is then added portionwise.

The temperature of the mixture is allowed to return to 20° C. and the mixture is left standing overnight. The mixture is poured into water, acidified and extracted with CH₂Cl₂. The organic phase is washed with water, dried, filtered and evaporated.

3-(Ethylthio)-5-fluoro-3-(2-hydroxyethyl)-1,3-dihydro-2(2H)-indolone tosylate is obtained. M.p. 105° C.

3-(Ethylthio)-5-fluoro-3-(2-[4-(7-methoxy-1,2,3,4-tetrahydro-1-naphthyl)-1-piperazinyl]ethyl-1,3-dihydro2(2H)-indolone.

A mixture of 8.1 g (0.0328 mole) of 1-(7-methoxy1,2,3,4-tetrahydro-1-naphthyl)piperazine and 6.7 g (0.0164 mole) of 3-(ethylthio)-5-fluoro-3-(2-hydroxyethyl)-1,3-dihydro-2(2H)-indolone is heated to 110° C. for 1 hour.

The mixture is cooled and purified by chromatography on silica (eluant: ethyl acetate/CH₂Cl₂, 50:50).

An oil is obtained, which is used in the crude state for the next stage of the synthesis. 5-Fluoro-3-{2-[4-(7-methoxy-1,2,3,4-tetrahydro-1-naphthyl)-1-piperazinyl]ethyl}1,3-dihydro-2(2H)-indolone fumarate.

4.7 g (0.01 mole) of the above derivative, dissolved in 100 ml of ethanol, is brought to reflux for 2 hours in the presence of 30 g of deactivated Raney nickel.

The nickel is filtered off and rinsed with ethanol and the filtrate is then evaporated.

5-Fluoro-3-{2-[4-(7-methoxy-1,2,3,4-tetrahydro-1-naphthyl)-1-piperazinyl]ethyl}-1,3-dihydro-2(2H)-indolone fumarate is prepared in an ethanol/ether mixture. M.p. 136° C.

EXAMPLE 7

5-Fluoro-3-{2-[4-(7-methoxy-1-naphthyl)-1-piperazinyl]ethyl}-1,3-dihydro-2(2H)-indolone 3-(Ethylthio)-5-fluoro-3-{2-[4-(7-methoxy-1-naphthyl)-1-piperazinyl]ethyl}-1,3-dihydro-2(2H)-indolone.

An intimate mixture of 3.66 g (0.0151 mole) of 1-(7-methoxy-1-naphthyl)piperazine and 3.09 g (0.00755 mole) of 3-(ethylthio)-5-fluoro-3-(2-hydroxyethyl)-1,3-dihydro-2(2H)indolone tosylate is heated to 130° C. for 45 minutes.

The reaction medium is then stirred between alkaline water and methylene chloride, settling is allowed to take place and the organic phase is separated and then washed and dried over magnesium sulphate.

After evaporation of the solvent, the residual oil is eluted with a methylene chloride/acetone (90:10) mixture on a column of 250 g of Merck 40 silica.

After concentration of the pure fractions, 2.8 g of a white solid are obtained, and this is ground in ether, then drained, washed and dried. 2.3 g of a white solid are finally obtained, the melting point of which is 180°–2° C.

5-Fluoro-3-{2-[4-(7-methoxy-1-naphthyl)-1-piperazinyl]-ethyl}-1,3-dihydro-2(2H)-indolone.

A suspension of 5 g of the above solid and 50 g of Raney nickel (deactivated beforehand with acetone) is heated under reflux for 3 hours in 350 ml of ethanol. After filtration of the catalyst and evaporation of the solvent, the remaining solid is partially dissolved in 2.2 l of ether. Some insoluble matter is filtered off and the filtrate is concentrated to approximately 60 ml and then left to stand in the refrigerator.

After several hours, the crystallized solid is drained, washed with ether and dried, and 3.27 g of a white solid of melting point 177°–8° C. are obtained.

EXAMPLE 8

5-Fluoro-3-{2-[4-(7-methoxy-1,2,3,4-tetrahydro-1-naphthyl)-1-piperazinyl]ethyl}-1,3-dihydro-2(2H)-indolone fumarate (dextrorotatory isomer)

3-(Ethylthio)-5-fluoro-3-{2-[4-(7-methoxy-1,2,3,4-tetrahydro-1-naphthyl)-1-piperazinyl]ethyl}-1,3-dihydro2(2H)-indolone (dextrorotatory isomer).

A mixture of 19.8 g (0.0803 mole) of the dextrorotatory isomer of 1-(7-methoxy-1,2,3,4-tetrahydro-1-naphthyl)piperazine and 16.3 g (0.0398 mole) of 3-(ethylthio)-5-fluoro-3-(2-hydroxyethyl)-1,3-dihydro-2(2H)-indolone tosylate in 140 ml of toluene is brought to the refluxing temperature for 2 h.

The mixture is stirred in the presence of ether and 2N sodium hydroxide. After settling has taken place and separation, the mixture is washed with water, dried and evaporated.

After chromatography on a silica column, using as eluant a $CH_2Cl_2$/methanol mixture from 98:2 to 98:4, 16.2 g of pure product are recovered.

5-Fluoro-3-{2-[4-(7-methoxy-1,2,3,4-tetrahydro-1-naphthyl)-1-piperazinyl]ethyl}-1,3-dihydro-2(2H)-indolone (dextrorotatory isomer).

106 g of Raney nickel in 700 ml of acetone are brought to the refluxing temperature for 2 h and the mixture is then washed with alcohol.

16 g (0.033 mole) of the compound obtained above, dissolved in 400 ml of ethanol, are then added. The mixture is brought to the refluxing temperature for 2 h. The nickel is filtered off and rinsed with ethanol and the filtrate is evaporated. The compound in base form melts at 114° C.

The fumarate of the compound obtained is prepared in a mixture of ethanol and ether. M.p. 132° C. $[\alpha]_D^{20} = 78.5°$ C. = 1.04 methanol.

EXAMPLE 9

5-Fluoro-3-{2-[4-(7-methoxy-1,2,3,4-tetrahydro-1-naphthyl)-1-piperazinyl]ethyl}-1,3-dihydro-2(2H)-indolone fumarate (laevorotatory isomer)

3-(Ethylthio)-5-fluoro-3-{2-[4-(7-methoxy-1,2,3,4-tetrahydro-1-naphthyl)-1-piperazinyl]ethyl}-1,3-dihydro2(2H)-indolone (laevorotatory isomer).

A mixture of 13.9 g (0.0564 mole) of the laevorotatory isomer of 1-(7-methoxy-1,2,3,4-tetrahydro-1naphthyl)piperazine, 20.06 g (0.0490 mole) of 3-(ethylthio)-5-fluoro-3-(2-hydroxyethyl)-1,3-dihydro-2(2H)-indolone tosylate and 9.4 g (0 112 mole) of sodium hydrogen carbonate in 155 ml of toluene is brought to 100° C. for 9 h on an oil bath.

The inorganic salts are filtered off and the filtrate is then evaporated.

After chromatography on a silica column with a 97:3 $CH_2Cl_2$/methanol mixture as eluant, 19.4 g of pure product are obtained. $[\alpha]_D^{20} = -81.5°$.

5-Fluoro-3-{2-[4-(7-methoxy-1,2,3,4-tetrahydro-1-naphthyl)-1-piperazinyl]ethyl}-1,3-dihydro-2(2H)-indolone (laevorotatory isomer).

127 g of Raney nickel are brought to boiling for 2 h in 850 ml of acetone. The acetone is separated after settling has taken place and washed twice with ethanol.

A solution of 19.3 g (0.04 mole) of the compound obtained above in 480 ml of absolute ethanol is added to this mixture. The mixture is brought to the refluxing temperature for 1 h while stirring vigorously The Raney nickel is filtered off, the filtrate is evaporated under vacuum and the mixture is taken up with ether. Some insoluble matter is filtered off. After evaporation, the product is obtained in base form.

The fumarate of this compound is prepared in an ethanol/ether mixture.

After recrystallization in propanol, the product melts at 132° C. $[\alpha]_D^{20} = -78.3°$ C. = 1.04 methanol.

APPENDIX $$AX + H-N\underset{\phantom{xx}}{\overset{\phantom{xx}}{\bigcirc}}N-COCalkyl$$
(II)   (III)

$$\downarrow$$

$$A-N\underset{\phantom{xx}}{\overset{\phantom{xx}}{\bigcirc}}N-COCalkyl$$
(I)

$$\downarrow$$

$$A-N\underset{\phantom{xx}}{\overset{\phantom{xx}}{\bigcirc}}N-H$$
(I)

We claim:

1. A compound, of the formula $$A-N\underset{\phantom{xx}}{\overset{\phantom{xx}}{\bigcirc}}N-R$$

in which
R is hydrogen or a straight or branched ($C_{1-4}$)alkoxycarbonyl group; and
A is a 7-methoxy-1-naphthalenyl, 6-methoxy-2,3-dihydro-1-(1H)-indenyl or 7-methoxy-1,2,3,4-tetrahydro-1naphthalenyl group, or an optically active isomer thereof, or a salt thereof.

2. A compound according to claim 1 which is:
1-(7-methoxy-1-naphthalenyl)piperazine,
1-[6-methoxy-2,3-dihydro-1-(1H)-indenyl]piperazine,
(±)-1-(7-methoxy-1,2,3,4-tetrahydro-1-naphthalenyl)piperazine,
(±)-1-(7-methoxy-1,2,3,4-tetrahydro-1-naphthalenyl)piperazine, or
(−)-1-(7-methoxy-1,2,3,4-tetrahydro-1-naphthalenyl)piperazine,
or a salt thereof.

3. A compound according to claim 1 in which the salt is a fumarate or mandelate salt.

* * * * *